(12) United States Patent
Kim et al.

(10) Patent No.: US 8,507,904 B2
(45) Date of Patent: Aug. 13, 2013

(54) COMPOUND INCLUDING INDOLE DERIVATIVE, ORGANIC ELECTRONIC ELEMENT USING SAME, AND TERMINAL THEREOF

(75) Inventors: Dongha Kim, Seongnam-si (KR); Jungcheol Park, Jinhae-si (KR); Jinuk Ju, Gyeongsangnam-do (KR); Jangyeol Baek, Sacheon-si (KR); Wonsam Kim, Seongnam-si (KR); Eunkyung Kim, Jinju-si (KR); Choi Paehyuk, Suwon (KR); Junghwan Park, Seoul (KR)

(73) Assignee: Duksan High Metal Co., Ltd., Ulsan (KR)

( * ) Notice: Subject to any disclaimer, the term of this patent is extended or adjusted under 35 U.S.C. 154(b) by 0 days.

(21) Appl. No.: 13/579,870

(22) PCT Filed: Jul. 12, 2010

(86) PCT No.: PCT/KR2010/004517
§ 371 (c)(1),
(2), (4) Date: Aug. 17, 2012

(87) PCT Pub. No.: WO2011/102573
PCT Pub. Date: Aug. 25, 2011

(65) Prior Publication Data
US 2012/0305906 A1 Dec. 6, 2012

(30) Foreign Application Priority Data
Feb. 19, 2010 (KR) .................. 10-2010-0014964

(51) Int. Cl.
*C07D 209/08* (2006.01)

(52) U.S. Cl.
USPC ............................................................ 257/40

(58) Field of Classification Search
USPC ............................................................ 257/40
See application file for complete search history.

(56) References Cited

U.S. PATENT DOCUMENTS

| | | | |
|---|---|---|---|
| 8,278,819 B2* | 10/2012 | Hosokawa et al. | 313/504 |
| 2004/0135167 A1* | 7/2004 | Nii | 257/103 |
| 2006/0083945 A1* | 4/2006 | Morishita et al. | 428/690 |
| 2006/0147747 A1 | 7/2006 | Yamamoto et al. | |
| 2007/0072002 A1 | 3/2007 | Kim et al. | |
| 2007/0160871 A1* | 7/2007 | Morishita et al. | 428/690 |
| 2010/0244006 A1* | 9/2010 | Ise et al. | 257/40 |
| 2012/0018717 A1 | 1/2012 | Kim et al. | |
| 2012/0080670 A1 | 4/2012 | Park et al. | |
| 2012/0168734 A1 | 7/2012 | Park et al. | |
| 2012/0273766 A1* | 11/2012 | Kato et al. | 257/40 |

FOREIGN PATENT DOCUMENTS

| | | |
|---|---|---|
| JP | 2001291590 A | 10/2001 |
| JP | 2003277743 A | 10/2003 |
| JP | 2003277744 A | 10/2003 |
| KR | 1020070034430 A | 3/2007 |

OTHER PUBLICATIONS

International Search Report (in Korean with English Translation) and Written Opinion (in Korean) for PCT/KR2010/004517, mailed Mar. 3, 2011; ISA/KR.

* cited by examiner

*Primary Examiner* — Eugene Lee
(74) *Attorney, Agent, or Firm* — Harness, Dickey & Pierce, P.L.C.

(57) ABSTRACT

Disclosed are a compound including an indole derivative, an organic electronic element using the same, and a terminal thereof.

11 Claims, 6 Drawing Sheets

COMPOUND INCLUDING INDOLE DERIVATIVE, ORGANIC ELECTRONIC ELEMENT USING SAME, AND TERMINAL THEREOF

TECHNICAL FIELD

The present invention relates to a compound including an indole derivative, an organic electronic element using the same, and a terminal thereof.

BACKGROUND ART

In general, an organic light emitting phenomenon indicates conversion of electric energy into light energy by means of an organic material. An organic electronic element using the organic light emitting phenomenon generally has a structure including an anode, a cathode, and an organic material layer interposed therebetween. Herein, in many cases, the organic material layer may have a multi-layered structure having respective different materials in order to improve efficiency and stability of an organic electronic element. For example, it may include a hole injection layer, a hole transport layer, an emitting layer, an electron transport layer, an electron injection layer, and the like.

Materials used as an organic material layer in an organic electronic element may be classified into a light emitting material and a charge transport material, for example, a hole injection material, a hole transport material, an electron transport material, an electron injection material, etc. according to their functions. Then, the light emitting material may be divided into a high molecular weight type and a low molecular weight type according to their molecular weight, and may be divided into a fluorescent material from electronic singlet excited states and a phosphorescent material from electronic triplet excited states according to their light emitting mechanism. Further, the light emitting material can be classified into a blue, green or red light emitting material and a yellow or orange light emitting material required for giving a more natural color, according to a light emitting color.

Meanwhile, when only one material is used as a light emitting material, an efficiency of a device is lowered owing to a maximum luminescence wavelength being shifted to a longer wavelength due to the interaction between the molecules, the deterioration of color purity and the reduction in luminous efficiency. Therefore, a host/dopant system can be used as the light emitting material for the purpose of enhancing the color purity and the luminous efficiency through energy transfer. It is based on the principle that if a small amount of a dopant having a smaller energy band gap than a host forming an emitting layer is mixed with the emitting layer, excitons which are generated in the emitting layer are transported to the dopant, thus emitting a light having a high efficiency. Here, since the wavelength of the host is shifted according to the wavelength of the dopant, a light having a desired wavelength can be obtained according the kind of the dopant.

In order to allow the organic electronic element to fully exhibit the above-mentioned excellent characteristics, a material constituting the organic material layer in the device, for example, a hole injection material, a hole transport material, a light emitting material, an electron transport material and an electron injection material should be essentially composed of a stable and efficient material. However, the development of a stable and efficient organic material layer material for the organic electronic element has not yet been fully realized. Accordingly, the development of new materials is continuously desired.

DETAILED DESCRIPTION OF THE INVENTION

Technical Problem

In order to solve the above-mentioned problems occurring in the prior art, through embodiments of the present invention, a compound including an indole derivative was found. Further, it was found that when applied in an organic electronic element, the compound can highly improve luminous efficiency, stability, and life span of the device.

Accordingly, an object of the present invention is to provide a compound including an indole derivative, an organic electronic element using the same, and a terminal thereof.

Technical Solution

In accordance with an aspect of the present invention, there is provided a compound represented by Formula below.

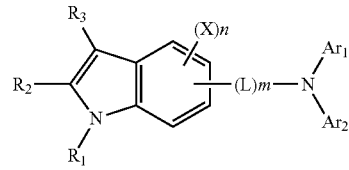

The inventive compound including an indole derivative is useful as a material for hole injection, hole transport, electron injection, electron transport, light emission, and/or passivation (capping), and especially, is useful alone as a light emitting material, a host, a dopant, a hole injection layer or a hole transport layer.

Also, the present invention provides an organic electronic element using the compound of Formula above, and a terminal including the organic electronic element.

Advantageous Effects

The inventive compound including an indole derivative may be useful as a material for hole injection, hole transport, electron injection, electron transport, light emission, and/or passivation (capping), and especially, may be useful alone as a light emitting material, a host, a dopant, a hole injection layer or a hole transport layer.

In an organic electronic element employing the compound, it is possible to achieve efficiency increase, driving voltage reduction, life span prolongation, and stability increase.

MODE FOR CARRYING OUT THE INVENTION

Figure 1:
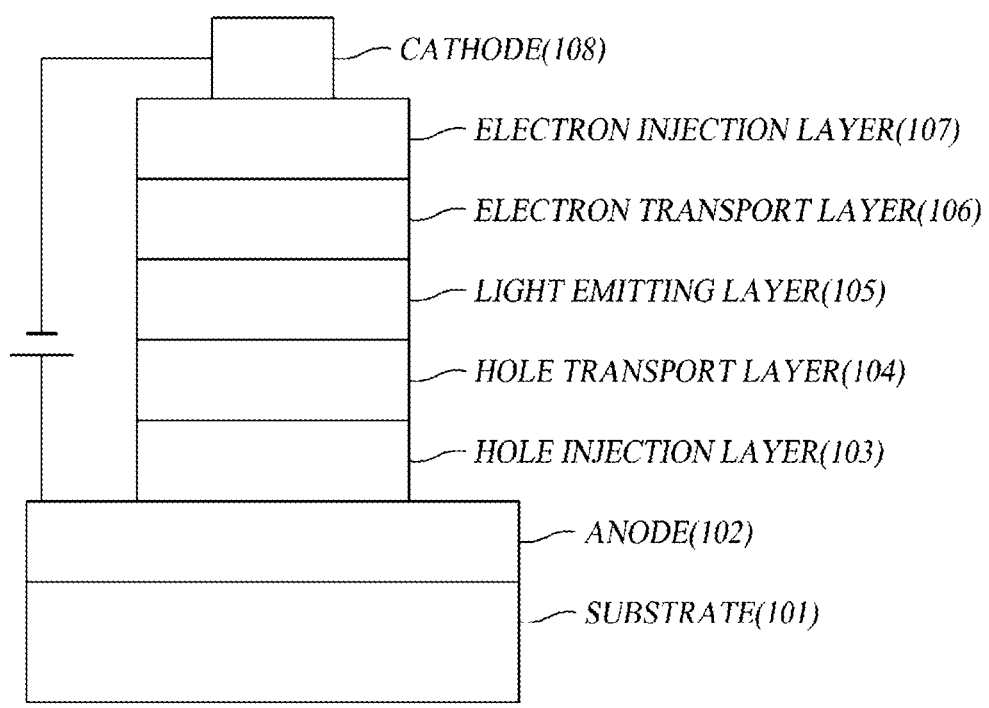
FIGS. 1 to 6 show examples of an organic electro-luminescence element which can employ a compound according to the present invention.

Hereinafter, exemplary embodiments of the present invention will be described with reference to the accompanying drawings. In designation of reference numerals to components in respective drawings, it should be noted that the same elements will be designated by the same reference numerals although they are shown in different drawings. Further, in the following description of the present invention, a detailed description of known functions and configurations incorporated herein will be omitted when it may make the subject matter of the present invention rather unclear.

In addition, terms, such as first, second, A, B, (a), (b) or the like may be used herein when describing components of the present invention. Each of these terminologies is not used to define an essence, order or sequence of a corresponding component but used merely to distinguish the corresponding component from other component(s). It should be noted that if it is described in the specification that one component is "connected," "coupled" or "joined" to another component, a third component may be "connected," "coupled," and "joined" between the first and second components, although the first component may be directly connected, coupled or joined to the second component.

The present invention provides a compound represented by Formula 1 below.

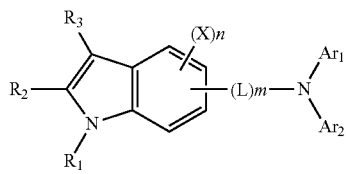

[Formula 1]

(1) R1 to R3 may be the same or different, and each may independently represent: a $C_6$~$C_{60}$ aryl group or a $C_5$~$C_{60}$ heterocyclic group substituted or unsubstituted with at least one selected from the group including hydrogen, a halogen group, a cyano group, a nitrile group, a $C_1$~$C_{60}$ alkyl group, a $C_1$~$C_{60}$ alkoxy group, a $C_1$~$C_{60}$ alkylamine group, a $C_1$~$C_{60}$ arylamine group, a $C_1$~$C_{60}$ alkylthiophene group, a $C_6$~$C_{60}$ arylthiophene group, a $C_2$~$C_{60}$ alkenyl group, a $C_2$~$C_{60}$ alkynyl group, a $C_3$~$C_{60}$ cycloalkyl group, a $C_6$~$C_{60}$ aryl group, a deuterium-substituted $C_6$~$C_{60}$ aryl group, a $C_8$~$C_{60}$ arylalkenyl group, a substituted or unsubstituted silane group, a substituted or unsubstituted boron group, a substituted or unsubstituted germanium group, and a substituted or unsubstituted $C_5$~$C_{60}$ heterocyclic group; an amino group substituted with at least one substituent selected from the group including a substituted or unsubstituted aryl group, a substituted or unsubstituted arylalkyl group, and a substituted or unsubstituted arylalkenyl group; a fused cyclic group of a $C_6$~$C_{60}$ aromatic ring with a $C_4$~$C_{60}$ aliphatic ring; or any group selected from the group consisting of a hydrogen atom, a halogen atom, a nitro group, a cyano group, a substituted or unsubstituted aliphatic hydrocarbon group, a substituted or unsubstituted aryl group, and a substituted or unsubstituted hetero aryl group.

(2) n may represent an integer of greater than 0, e.g., an integer of 1 to 3.

(3) X may be the same as R1 to R3, wherein X, and R1 to R3 may form a ring, e.g., an aliphatic or hetero fused ring together with an adjacent group.

(4) Ar1 to Ar2 may be the same or different, and each may be independently selected from the group including: a $C_1$~$C_{60}$ alkyl group, a $C_1$~$C_{60}$ alkoxy group, a $C_1$~$C_{60}$ aryl group, a carbazolyl group, or a fluorenyl group, substituted or unsubstituted with at least one substituent selected from the group including a halogen group, an alkyl group, an alkenyl group, a substituted or unsubstituted aryl group, a substituted or unsubstituted arylalkyl group, a substituted or unsubstituted arylalkenyl group, a substituted or unsubstituted hetero cyclic group, a substituted or unsubstituted carbazolyl group, a substituted or unsubstituted fluorenyl group, a nitrile group, and an acetylene group, or a hetero cyclic group that is substituted or unsubstituted with at least one substituent selected from the group including a halogen group, an alkyl group, an alkenyl group, an alkoxy group, a substituted or unsubstituted arylamine group, a substituted or unsubstituted aryl group, a substituted or unsubstituted carbazolyl group, a substituted or unsubstituted fluorenyl group, a nitrile group, and an acetylene group and includes O, N, or S as a heteroatom; a hydroxyl group; a carboxyl group; a nitrile group, a nitro group, a halogen group, —N(R')(R''); —CO—N(R')(R''); and —COOR'. Herein, these may form an aliphatic or hetero fused ring together with an adjacent group.

(5) L may represent a substituted or unsubstituted arylene group, a substituted or unsubstituted hetero arylene group, a group selected from the group including divalent or trivalent, substituted or unsubstituted aliphatic hydrocarbons, or a divalent linking group, and m may represent an integer of greater than 0, e.g., an integer of 0 to 3.

The compound represented by Formula 1 may be used in a soluble process so as to form an organic material layer. In other words, the organic material layer that will be described later may be formed in such a manner that it includes the compound through the soluble process.

Hereinafter, Synthesis Examples, Comparative Examples and Examples on some of specific compounds in the case of m=0 or m=1 in Formula 1 will be exemplified. Further, through the Examples, it is possible to expect specific compounds in the case of m≧2, and also Synthesis Examples and Comparative Examples thereof.

In Formula 1 above, when L is a simple linking group, the compound may be represented by Formula 2 below.

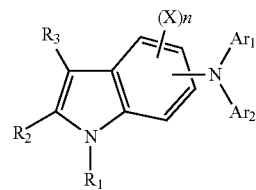

[Formula 2]

Unlike this, in Formula 1 above, when L has a substituted or unsubstituted group, the compound may be represented by Formula 3 below.

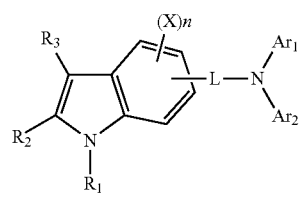

[Formula 3]

Specific examples of a compound including an indole derivative according to one embodiment of the present invention, represented by Formulas 1 to 3, may include compounds represented by Formula 4 below. However, the present invention is not limited thereto.

[Formula 4]
A-1
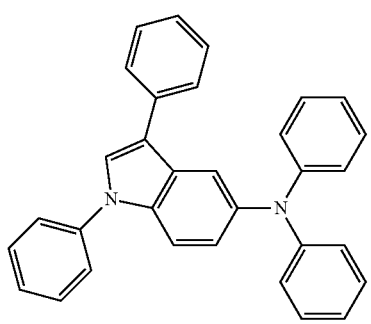
A-2
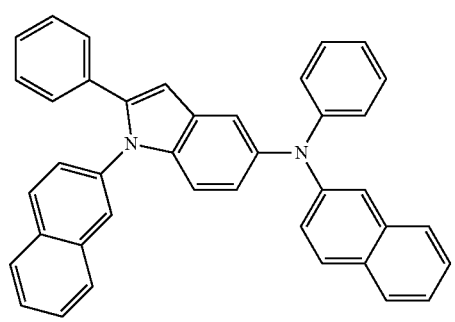
A-3
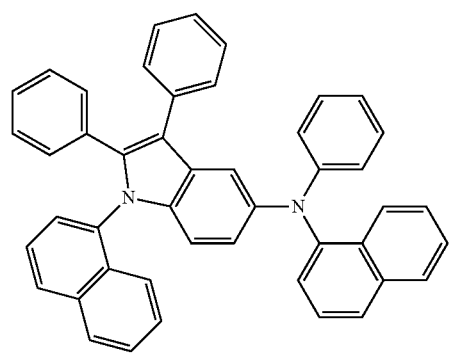
A-4
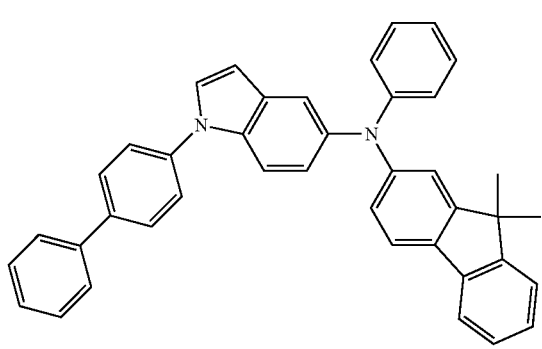
-continued
A-5
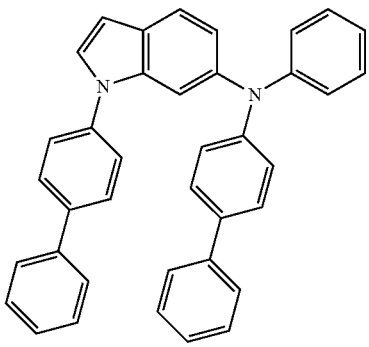
A-6
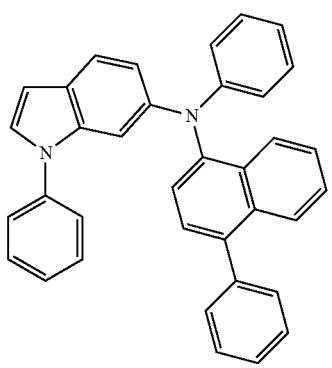
A-7
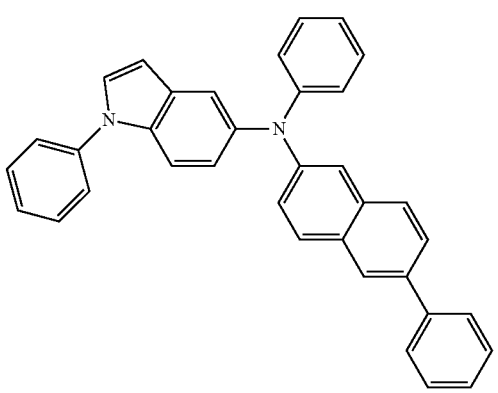
A-8
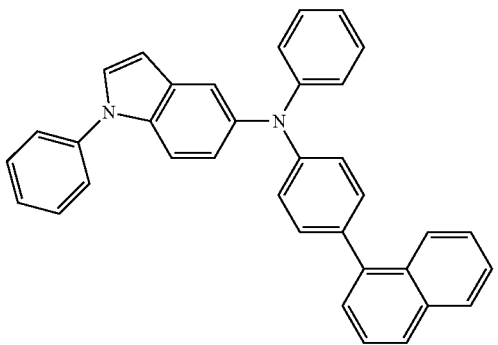

A-9
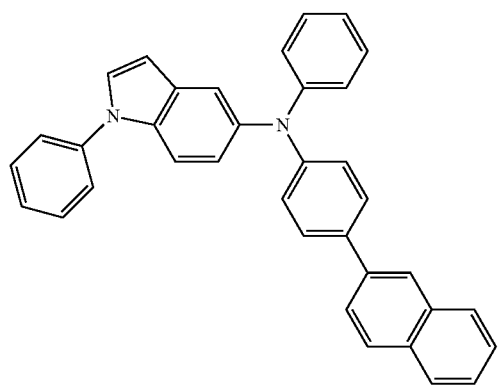
A-11
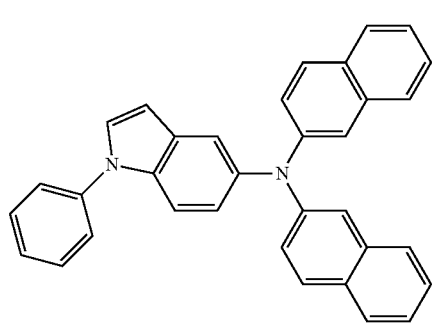
A-12
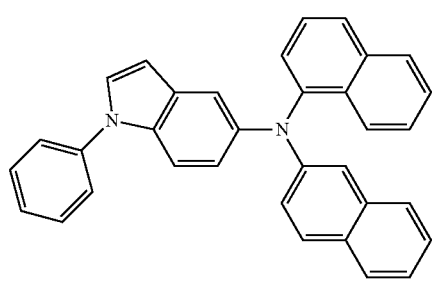
A-13
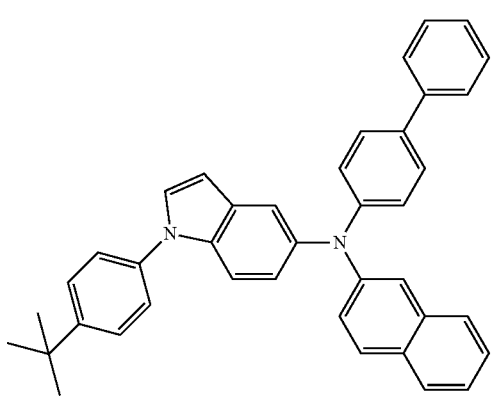
A-14
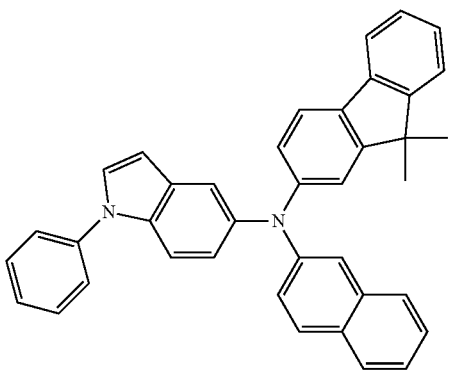
A-15
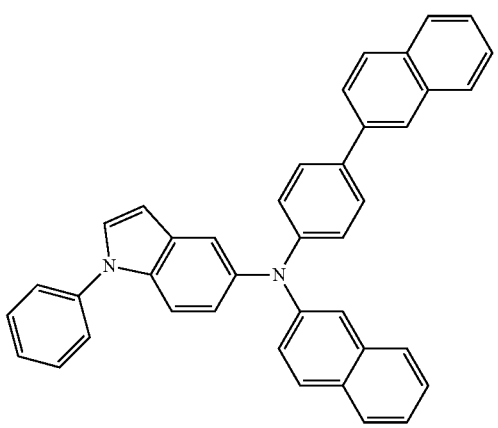
A-16
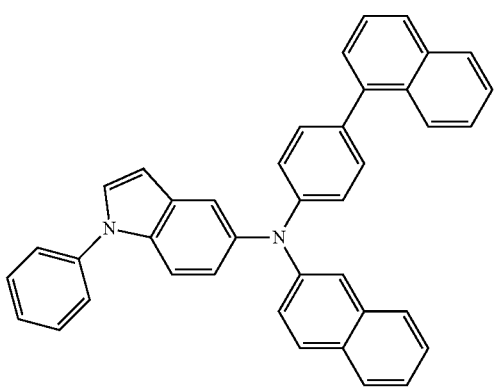
A-17
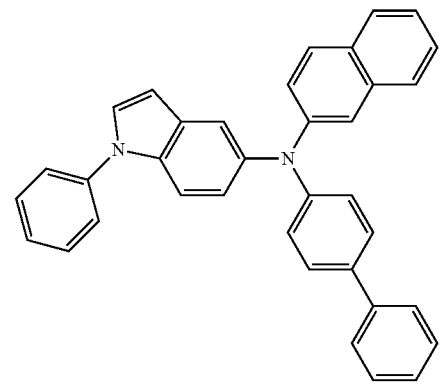

A-18
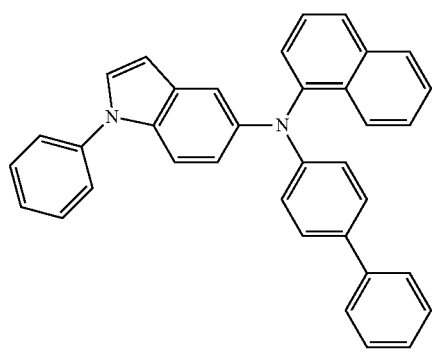
A-19
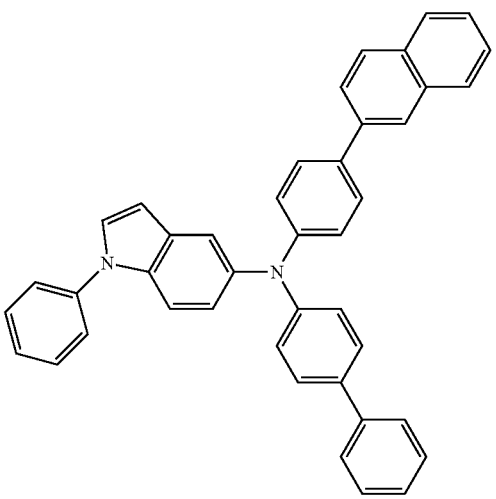
A-20
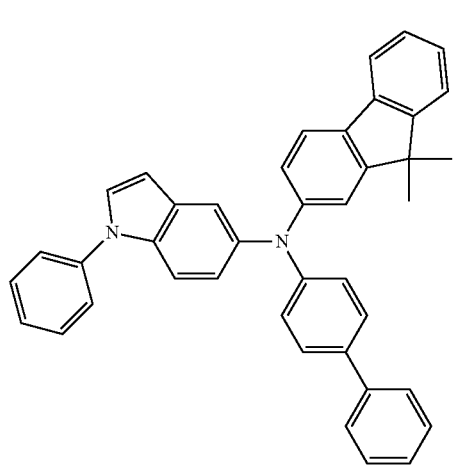
A-21
A-22
A-23
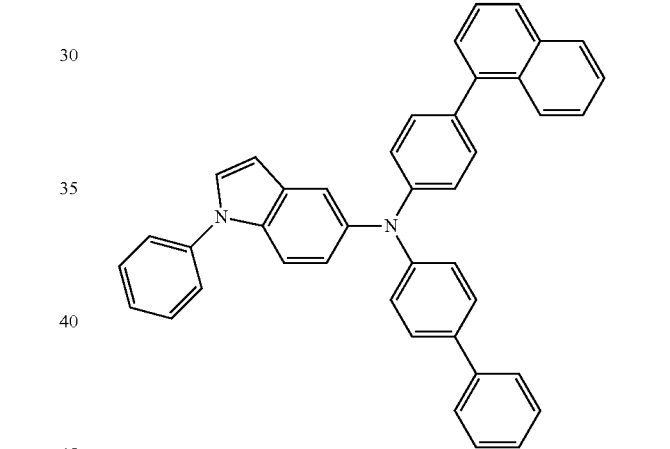

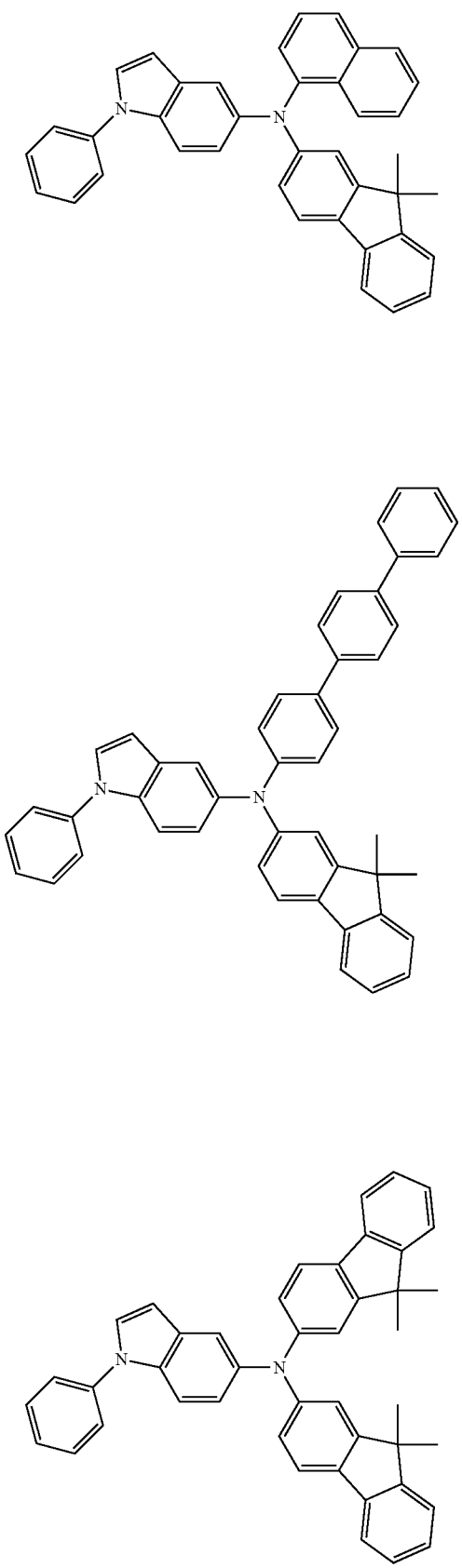
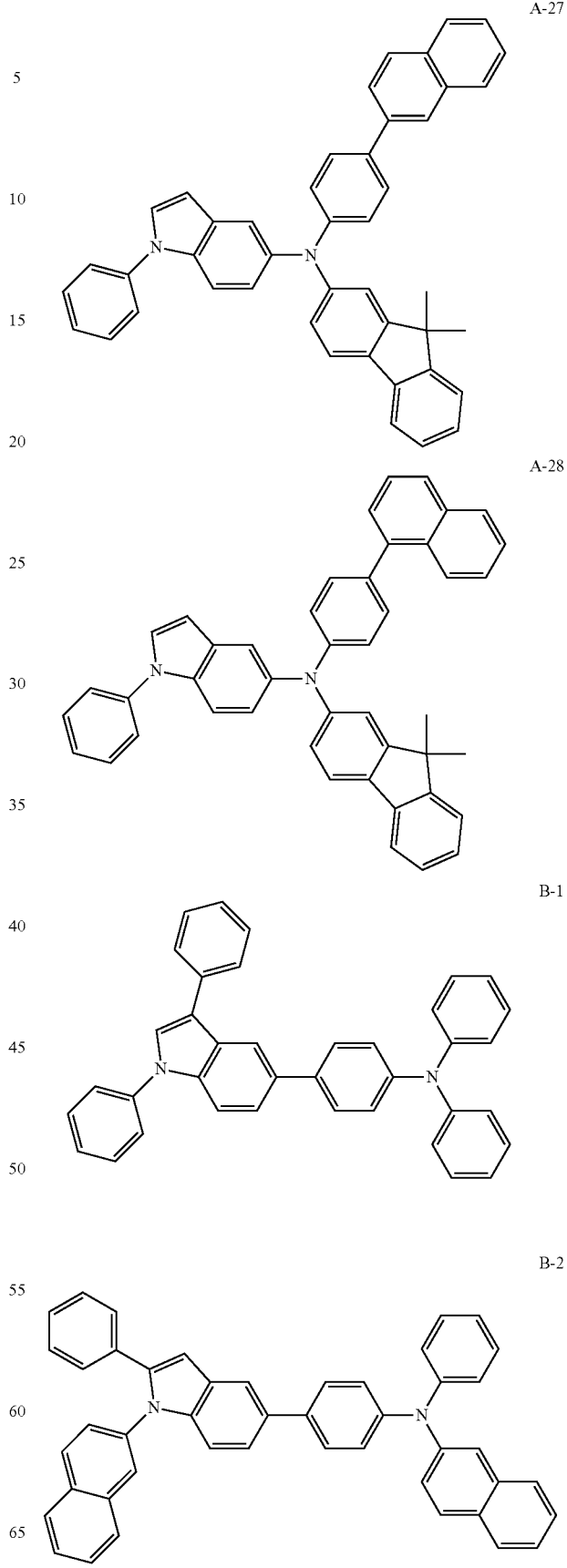

B-3
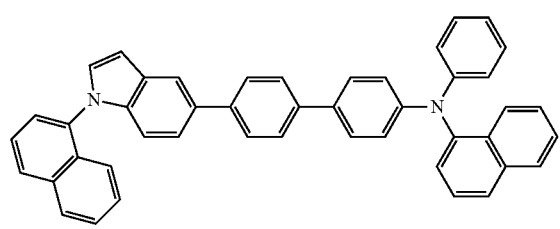
B-4
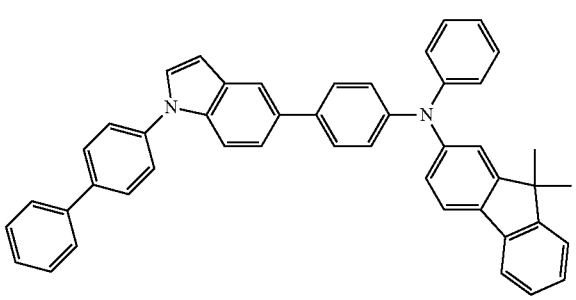
B-5
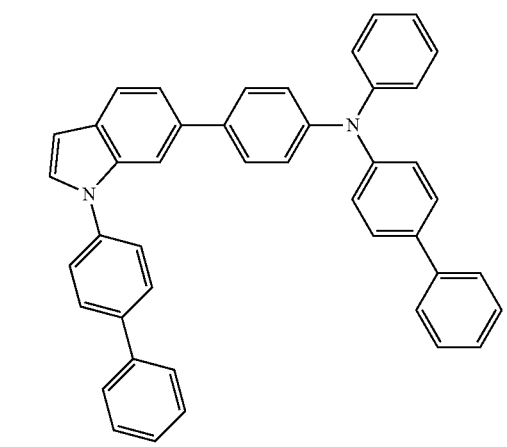
B-6
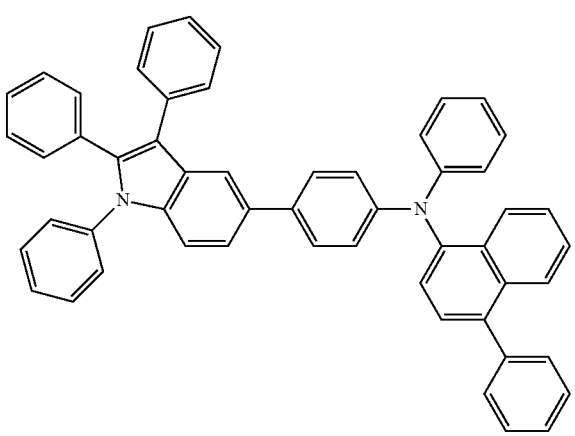
B-7
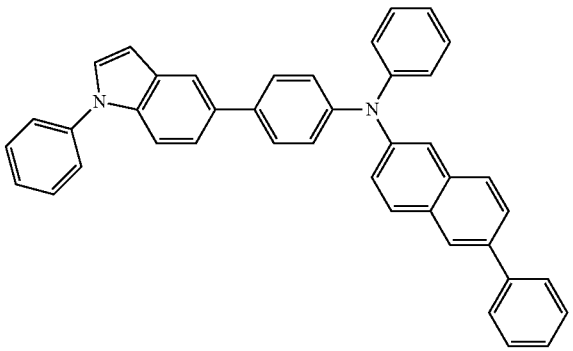
B-8
B-9
B-11
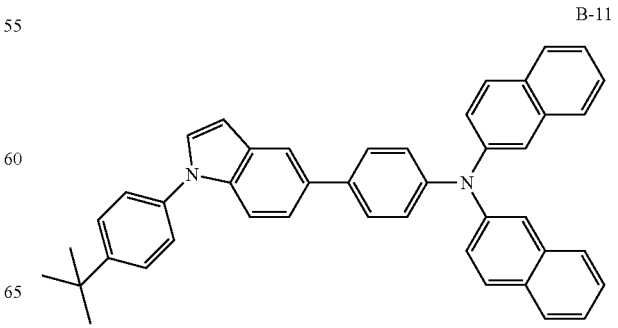

B-12
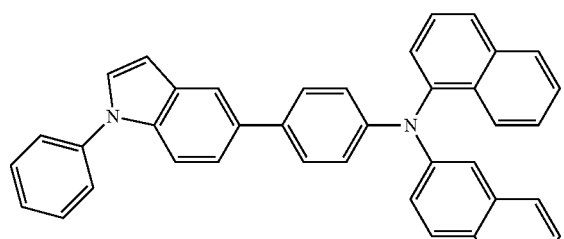
B-13
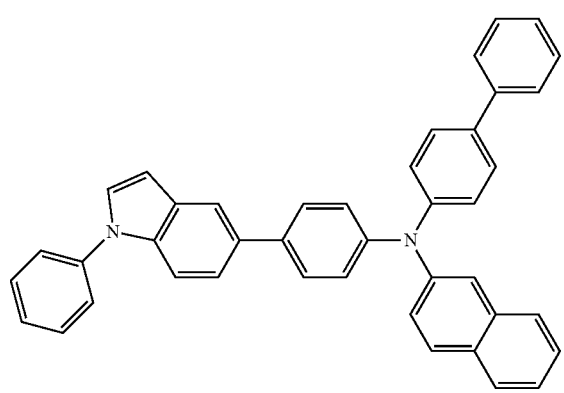
B-14
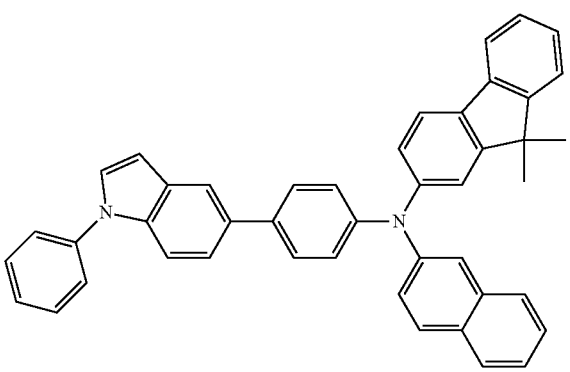
B-15
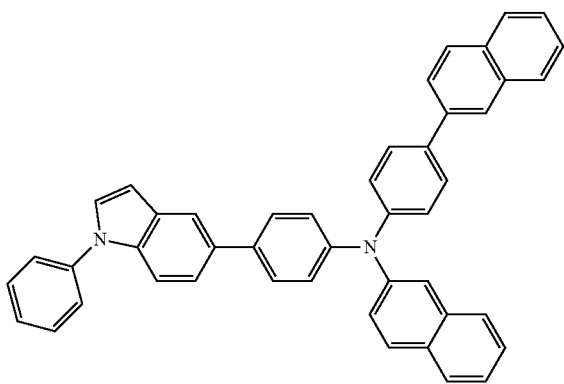
B-16
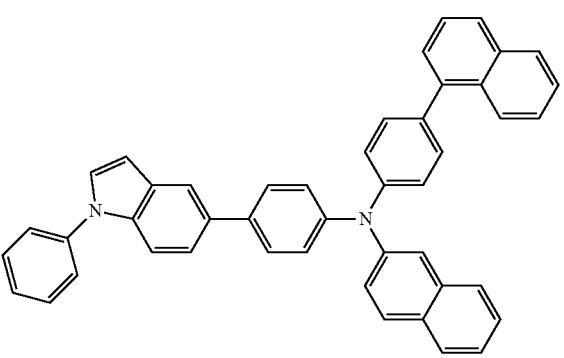
B-17
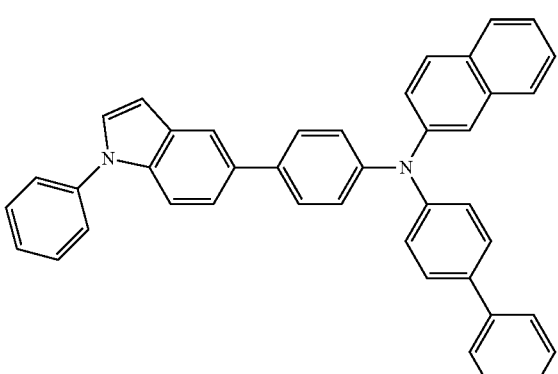
B-18
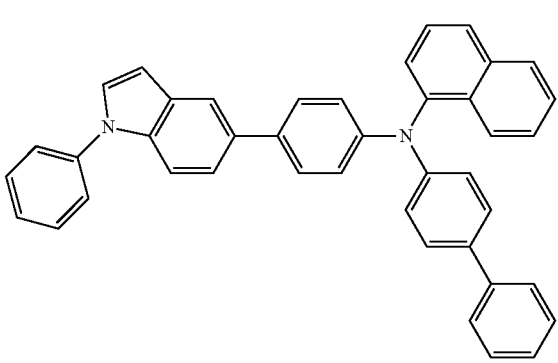
B-19
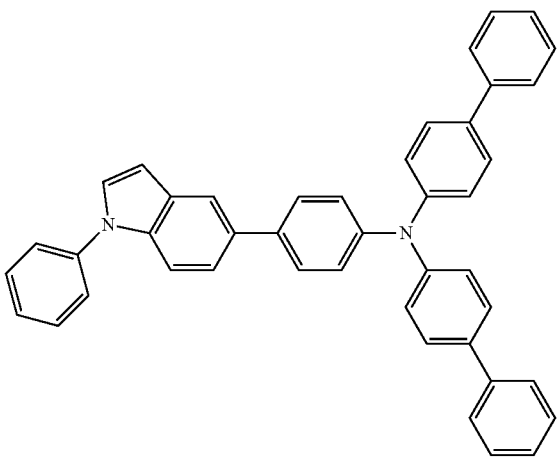

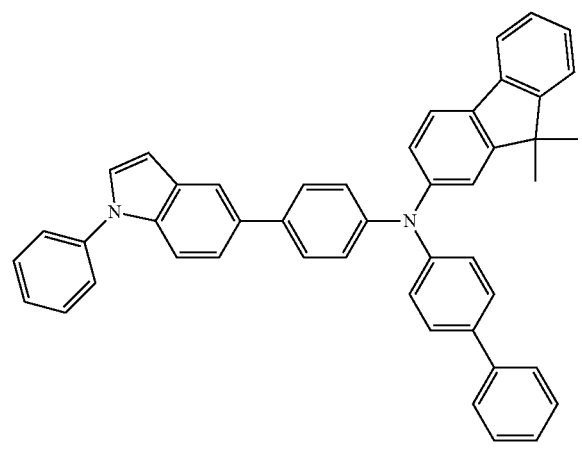
B-20
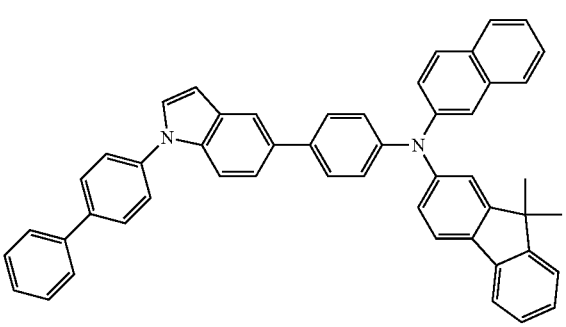
B-23
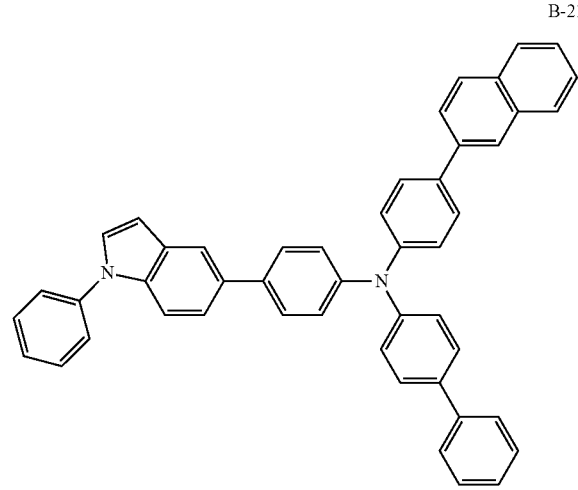
B-21
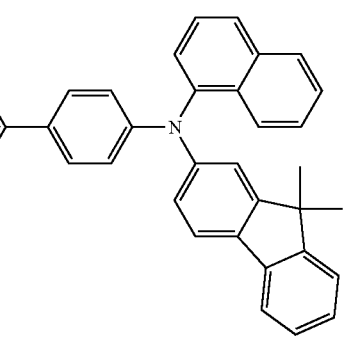
B-24
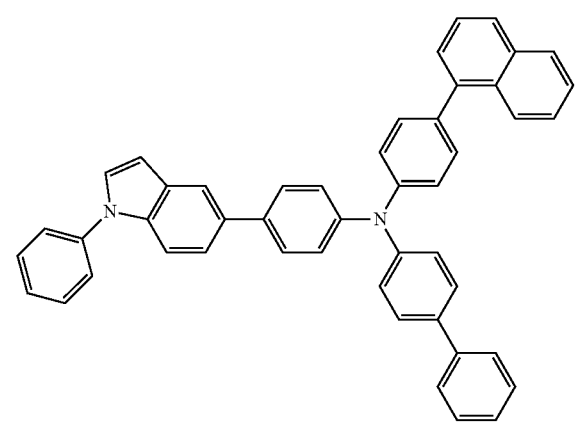
B-22
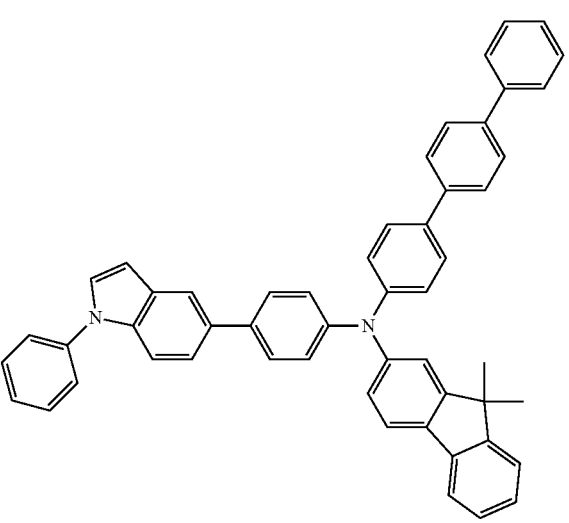
B-25

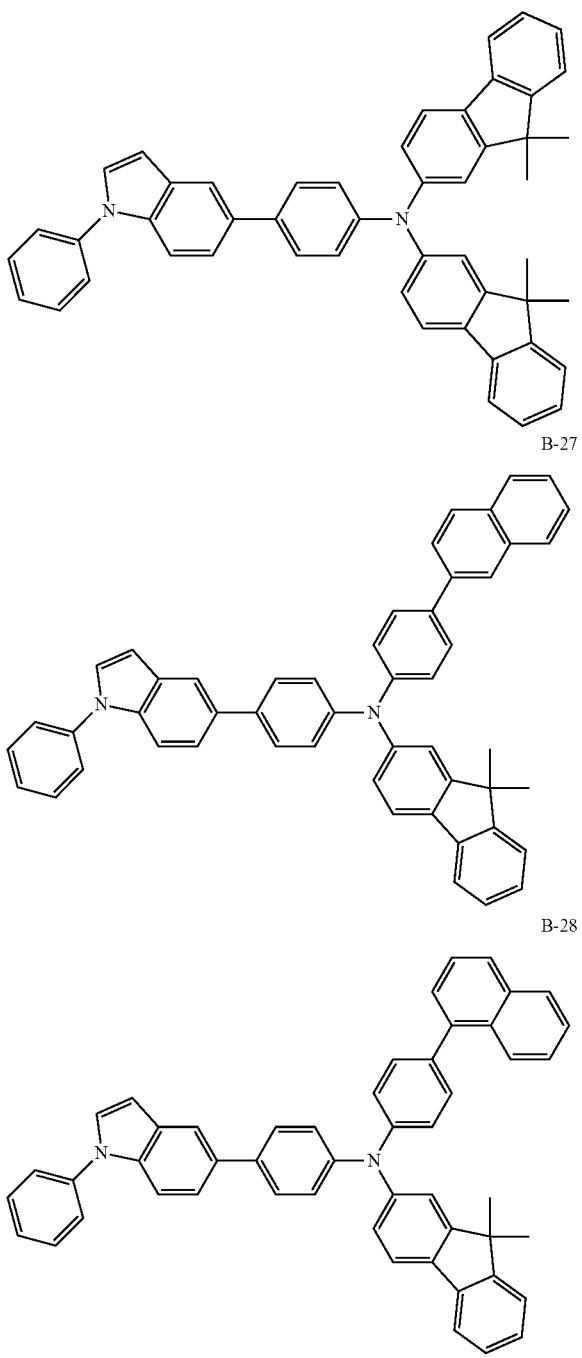

There are various organic electronic elements employing the compounds including the indole derivative, as described with reference to Formulas 1 to 4, as organic material layers. The organic electronic element in which the compounds including the indole derivative, as described with reference to Formulas 1 to 4, can be employed may include, for example, an organic light emitting diode (OLED), an organic solar cell, an organic photo conductor (OPC) drum, an organic transistor (organic TFT), and the like.

As one example of the organic electronic elements in which compounds including the indole derivative, as described with reference to Formulas 1 to 4, can be used, an organic light-emitting diode (OLED) will be described below, but the present invention is not limited thereto. The above described compounds may be applied to various organic electronic elements.

In another embodiment of the present invention, there is provided an organic electro-luminescence element as an organic electronic element including a first electrode, a second electrode, and an organic material layer interposed between these electrodes, in which at least one of organic material layers includes the compounds represented by Formulas 1 to 4.

Figure 2:
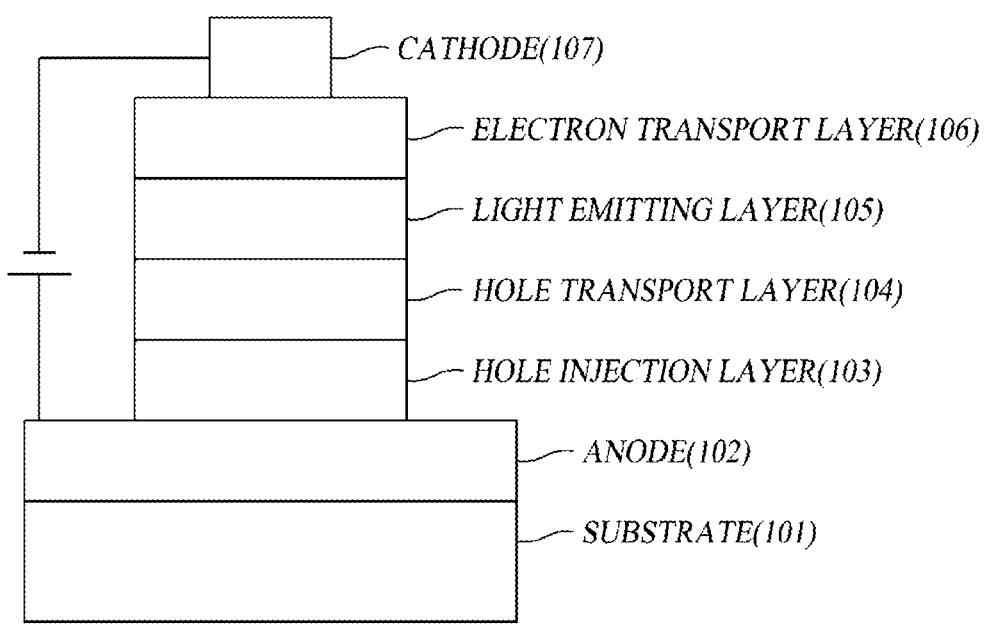
Figure 3:
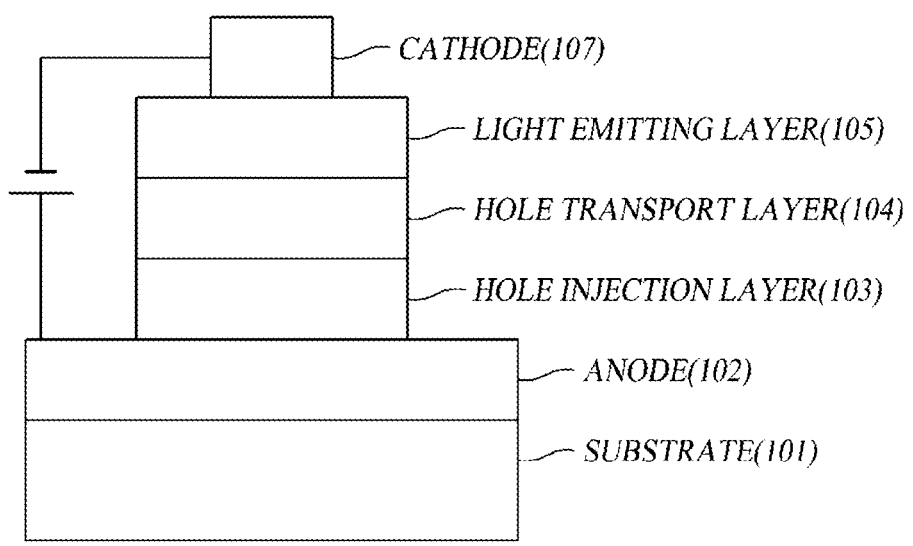
Figure 4:
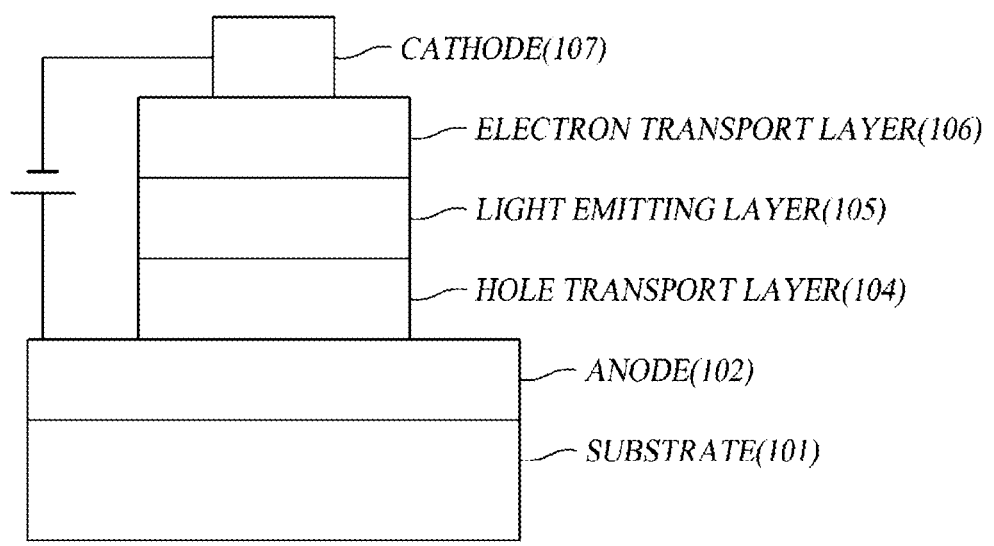
Figure 5:
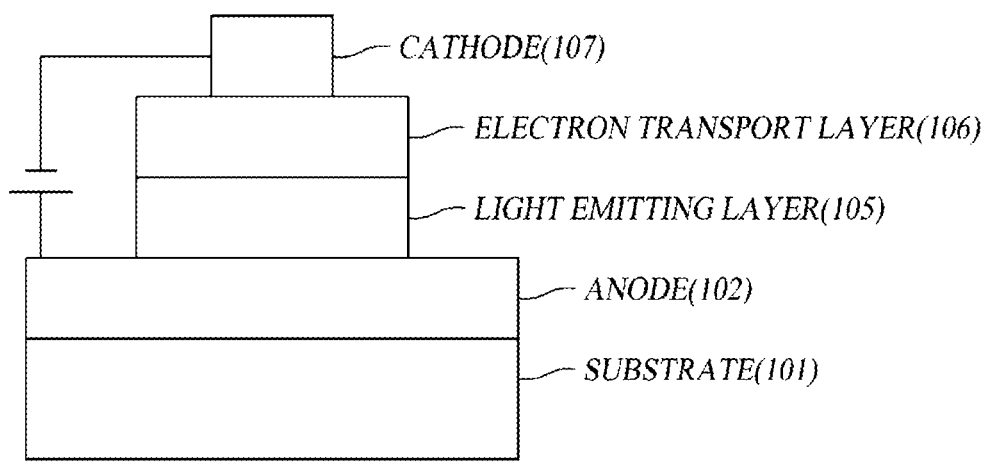
Figure 6:
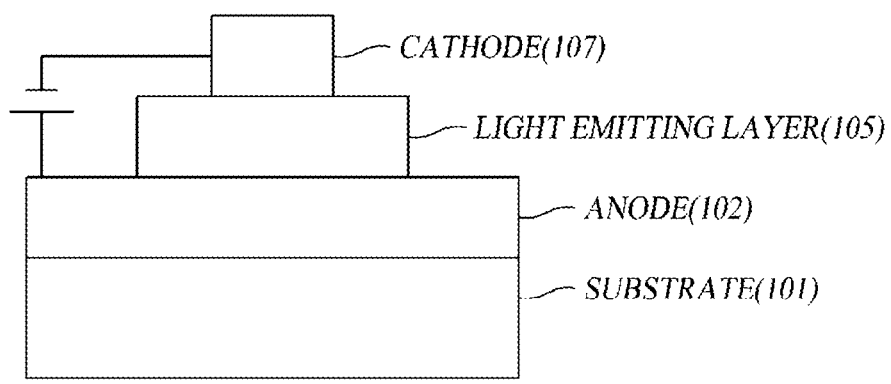

FIGS. 1 to 6 show examples of an organic electro-luminescence element which can employ a compound according to the present invention.

The organic electro-luminescence element according to another embodiment of the present invention may be manufactured by means of a manufacturing method and materials conventionally known in the art in such a manner that it can have a conventionally known structure, except that at least one of organic material layers including a hole injection layer, a hole transport layer, an emitting layer, an electron transport layer, and an electron injection layer is formed in such a manner that it can include the compounds represented by Formulas 1 to 4.

The structures of the organic electro-luminescence element according to another embodiment of the present invention are shown in FIGS. 1 to 6, but the present invention is not limited to the structures. Herein, the reference numeral 101 indicates a substrate, 102 indicates an anode, 103 indicates a hole injection layer (HIL), 104 indicates a hole transport layer (HTL), 105 indicates an emitting layer (EML), 106 indicates an electron injection layer (EIL), 107 indicates an electron transport layer (ETL), and 108 indicates a cathode. Although not shown, such an organic electro-luminescence element may further include a hole blocking layer (HBL) for blocking movement of holes, an electron blocking layer (EBL) for blocking movement of electrons, an emission assisting layer for supporting or assisting light emission, and a protective layer. The protective layer may be formed in such a manner that it, as an uppermost layer, can protect an organic material layer or a cathode.

Herein, the compound including the indole derivative, as described with reference to Formulas 1 to 4, may be included in at least one of organic material layers including a hole injection layer, a hole transport layer, an emitting layer, and an electron transport layer. Specifically, the compound including the indole derivative, as described with reference to Formulas 1 to 4, may be substituted for at least one of a hole injection layer, a hole transport layer, an emitting layer, an electron transport layer, an electron injection layer, a hole blocking layer, an electron blocking layer, an emission assisting layer, and a protective layer, or may be used in combination with these layers so as to form a multi-layered structure. Of course, the compound may be used for not only one layer of the organic material layers but also two or more layers.

Especially, the compound including the indole derivative, as described with reference to Formulas 1 to 4, may be used as a material for hole injection, hole transport, electron injection, electron transport, light emission, and passivation (capping). Especially, it may be used alone as a light emitting material, a host or a dopant in host/dopant.

For example, in manufacturing of the organic electro-luminescence element according to another embodiment of the present invention, a metal, a conductive metal oxide, or an alloy thereof may be deposited on a substrate by means of PVD (physical vapor deposition) such as sputtering or e-beam evaporation, so as to form an anode, and then an organic material layer including a hole injection layer, a hole transport layer, an emitting layer, an electron transport layer, and an electron injection layer may be formed thereon, and a material capable of being used as a cathode may be deposited thereon.

Besides, on a substrate, a cathode material, an organic material layer, and an anode material may be sequentially deposited so as to provide an organic electronic element. The organic material layer may be formed in a multi-layered structure including a hole injection layer, a hole transport layer, an emitting layer, an electron transport layer, and an electron injection layer, but the present invention is not limited thereto. It may be formed in a single layer structure. Further, the organic material layer may be manufactured with a smaller number of layers by using various polymer materials by means of a solvent process (e.g., spin coating, dip coating, doctor blading, screen printing, inkjet printing, or thermal transfer) instead of deposition.

In the organic electro-luminescence element according to another embodiment of the present invention, the above described compound including an indole derivative may be used in a soluble process such as a spin coating process or an ink jet process.

The substrate is a support for the organic electro-luminescence element, and may employ a silicon wafer, a quartz or glass plate, a metal plate, a plastic film or sheet.

On the substrate, an anode is positioned. Such an anode allows holes to be injected into a hole injection layer positioned thereon. As an anode material, a material having a high work function is preferably used so that injection of holes into an organic material layer can be smoothly carried out. Specific examples of an anode material that may be used in the present invention may include: metals (such as vanadium, chromium, copper, zinc, gold) or alloys thereof; metal oxides such as zinc oxide, indium oxide, indium tin oxide (ITO), indium zinc oxide (IZO); a metal-oxide combination such as ZnO:Al or $SnO_2$:Sb; and conductive polymers such as poly (3-methylthiophene), poly[3,4-(ethylene-1,2-dioxy) thiophene](PEDT), polypyrrole and polyaniline, but the present invention is not limited thereto.

On the anode, a hole injection layer is positioned. A material for such a hole injection layer is required to have a high efficiency for injecting holes from an anode, and to be able to efficiently transport the injected holes. For this, the material has to have a low ionization potential, a high transparency in visible rays, and a high stability for holes.

As a hole injection material, a material into which holes can be efficiently injected from an anode at a low voltage is used. HOMO (highest occupied molecular orbital) of the hole injection material preferably ranges from a work function of an anode material to HOMO of adjacent organic material layers. Specific examples of the hole injection material may include metal porphyrine-, oligothiophene-, and arylamine-based organic materials, hexanitrile hexaazatriphenylene- and quinacridone-based organic materials, perylene-based organic materials, and anthraquinone-, polyaniline-, and polythiophene-based conductive polymers, but the present invention is not limited thereto.

On the hole injection layer, a hole transport layer is positioned. Such a hole transport layer receives holes transferred from the hole injection layer and transfers them to an organic emitting layer positioned thereon. Further, the hole transport layer has a high hole mobility and a high hole stability and performs a role of blocking electrons. Besides these general requirements, it requires heat-resistance for a device when applied for an automobile display, and thus is preferably made of a material having a glass transition temperature (Tg) of 70° C. or more. The examples of a material satisfying these conditions may include NPD (or NPB), spiro-arylamine-based compound, perylene-arylamine-based compound, aza-cycloheptatriene compound, bis(diphenylvinylphenyl)an-thracene, silicongermaniumoxide compound, silicon-based arylamine compound, and the like.

On the hole transport layer, an organic emitting layer is positioned. Such an organic emitting layer is made of a material having a high quantum efficiency, in which holes and electrons which are injected from an anode and a cathode, respectively, are recombined so as to emit light. As a light emitting material, a material allowing holes and electrons transferred from a hole transport layer and an electron transport layer, respectively, to be combined so as to emit light in a visible ray range is used. Preferably, a material having a high quantum efficiency for fluorescence or phosphorescence may be used.

As a material or a compound satisfying these conditions, for a green color, Alq3 may be used, and for a blue color, Balq(8-hydroxyquinoline beryllium salt), DPVBi(4,4'-bis(2,2-diphenylethenyl)-1,1'-biphenyl) based material, Spiro material, spiro-DPVBi(Spiro-4,4'-bis(2,2-diphenylethenyl)-1,1'-biphenyl), LiPBO(2-(2-benzoxazoyl)-phenol lithium salt), bis(diphenylvinylphenylvinyl)benzene, aluminum-quinoline metal complex, imidazole, thiazol and oxazole-metal complex, or the like may be used. In order to improve the luminous efficiency of a blue color, perylene, and BczVBi (3,3'[(1,1'-biphenyl)-4,4'-diyldi-2,1-ethenediyl]bis(9-ethyl)-9H-carbazole; DSA(distrylamine)) may be doped in a small amount. For a red color, a green light emitting material may be doped with DCJTB([2-(1,1-dimethylethyl)-6-[2-(2,3,6,7-tetrahydro-1,1,7,7-tetramethyl-1H,5H-benzo(ij)quinolizin-9-yl)ethenyl]-4H-pyran-4-ylidene]-propanedinitrile) in a small amount. When a process such as inkjet printing, roll coating, spin coating, is used to form an emitting layer, a polymer such as polyphenylenevinylene (PPV)-based polymer or poly fluorene may be used for an organic emitting layer.

On the organic emitting layer, an electron transport layer is positioned. Such an electron transport layer requires a material which has a high efficiency for electrons injected from a cathode positioned thereon, and can efficiently transport the injected electrons. For this, a material having a high electron affinity, a high electron mobility, and a high electron stability is required. Specific examples of an electron transport material satisfying these conditions may include Al complex of 8-hydroxyquinoline; complex including $Alq_3$; organic radical compound; and hydroxyflavone-metal complex, but the present invention is not limited thereto.

On the electron transport layer, an electron injection layer is layered. The electron injection layer may be manufactured by using a metal complex compound (such as Balq, Alq3, Be(bq)2, Zn(BTZ)2, Zn(phq)2, PBD, spiro-PBD, TPBI, and Tf-6P) or a low molecular material including an aromatic compound having an imidazole ring or a boron compound. Herein, the electron injection layer may be formed in a thickness range of 100 Å to 300 Å.

On the electron injection layer, a cathode is positioned. Such a cathode performs a role of injecting electrons. As a material for the cathode, the same material as that used for an anode may be used. In order to achieve efficient electron injection, a metal having a low work function is more preferably used. Especially, metals such as tin, magnesium, indium, calcium, sodium, lithium, aluminum, silver, or alloys thereof may be used. Further, a double-layered electrode (e.g., lithium fluoride and aluminum, lithium oxide and aluminum, and strontium oxide and aluminum) with a thickness of 100 μm or less may be used.

As described above, the compound including the indole derivative, as described with reference to Formulas 1 to 4, may be used as a hole injection material, a hole transport material, a light emitting material, an electron transport material and an electron injection material, which are appropriate for fluorescent and phosphorescent elements of all colors (such as red, green, blue, white). Also, the compound may be used as a material of a host (or a dopant) of various colors.

The organic electro-luminescence element according to the present invention may be manufactured in a front luminescent type, a rear luminescent type, or a both-side luminescent type according to its materials.

Meanwhile, the present invention provides a terminal which includes a display device and a control part for driving the display device, the display device including the above described organic electronic element. The terminal means a wired/wireless communication terminal which is currently used or will be used in the future. The above described terminal according to the present invention may be a mobile communication terminal such as a cellular phone, and may include all kinds of terminals such as a PDA, an electronic dictionary, a PMP, a remote control, a navigation unit, a game player, various kinds of TVs, and various kinds of computers.

Example

Hereinafter, the present invention will be described more specifically with reference to Preparation Examples and Test Examples. However, the following examples are only for illustrative purposes and are not intended to limit the scope of the invention.

Preparation Example

Hereinafter, Preparation Examples or Synthesis Examples of the compounds including the indole derivative, included in Formula 4, will be described. However, since there are many compounds including an indole derivative, included in Formula 4, only one compound or two compounds from among the compounds will be exemplified. A person skilled in the art of the invention should realize that other compounds including an indole derivative can be prepared through Preparation Examples as described below although they are not exemplified.

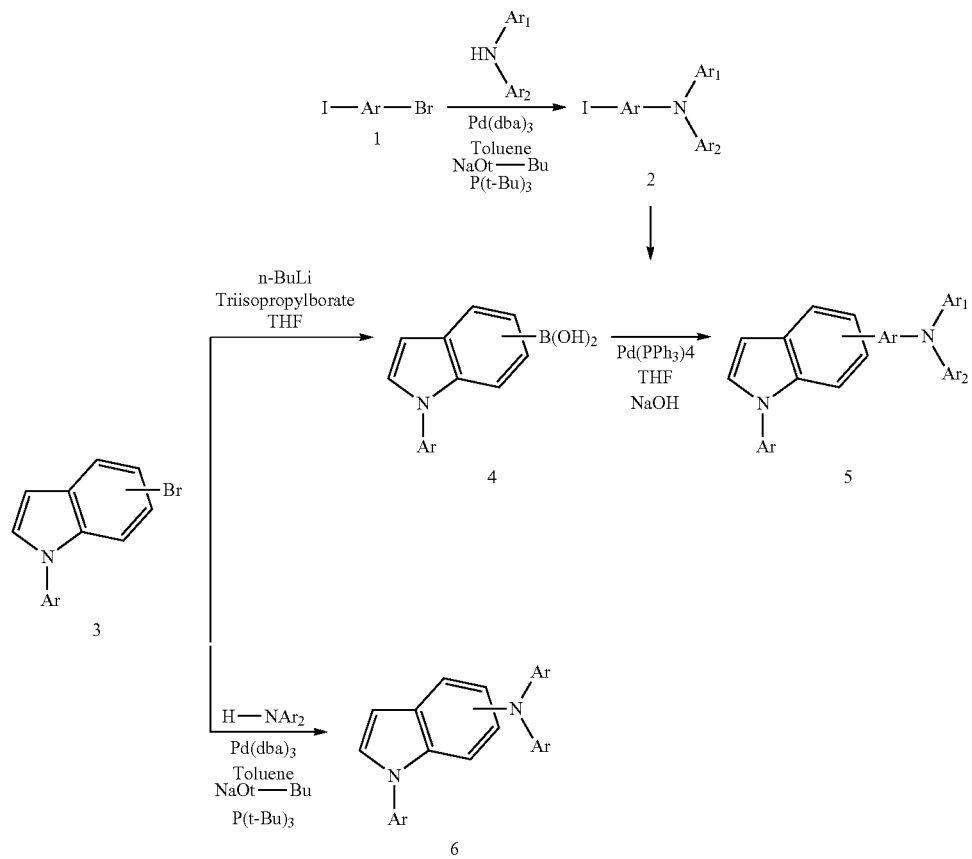

Synthesis Method of Intermediate 2

Dibiphenyl-4-ylamine, 1-Bromo-4-iodobenzene, Pd$_2$(dba)$_3$, Triphenylphosphine, and Sodiumtert-butoxide were dissolved in toluene solvent, and stirred under reflux at 130° C. for 24 hours. After the reaction was completed, the resultant product was extracted with MC and water, and dried and concentrated with MgSO$_4$. Then, the produced compound was purified with column chromatography so as to provide a required compound, intermediate 2 (yield: 68%).

Synthesis Method of Intermediate 4

Intermediate 3 was dissolved in THF, and at −78° C., n-BuLi was slowly dropped thereto, followed by stirring for about 1 hour. Then, triisopropylborate was slowly dropped thereto at −78° C., followed by stirring. The resultant product was acidified with 1N HCl, extracted with water and EA, and dried with MgSO$_4$. Then, through recrystallization with hexane, the intermediate 4 was obtained (yield: 54%).

Synthesis Method of Compound B-20 (Compound 5)

Phenylboronic acid, intermediate 4, and Pd(PPh$_3$)$_4$ were dissolved in 500 ml of THF, and 250 ml of water, and K$_2$CO$_3$ was added thereto. The resultant solution was heated under reflux for 24 hours. The obtained solid was washed with water and methanol, and purified by silica gel column chromatography to give a white solid, compound 5 (yield: 71%).

Synthesis Method of Compound A-26 (Compound 6)

A white solid, compound 6, was obtained (yield: 65%) in which the same method as described in the synthesis method of intermediate 4 was used except that in the synthesis method of intermediate 2, N-(biphenyl-4-yl)-9,9-dimethyl-9H-fluoren-2-amine was used instead of Dibiphenyl-4-ylamine, and intermediate 3 was used instead of 1-Bromo-4-iodobenzene.

Fabrication Test of Organic Electro-Luminescence Device

An organic electro-luminescence element was manufactured through a conventional method by using the synthesized compounds as a light emitting host material of an emitting layer or as a hole transport layer. First, on an ITO layer (anode) formed on a glass substrate, a copper phthalocyanine (hereinafter, referred to as CuPc) film as a hole injection layer was vacuum-deposited with a thickness of 10 nm.

Then, for measurement as a green host, on this film, 4,4-bis[N-(1-naphthyl)-N-phenylamino]biphenyl (hereinafter, referred to as a-NPD) as a hole transport compound was vacuum-deposited with a thickness of 30 nm so as to form a hole transport layer. After the hole transport layer was formed, for the measurement on the hole transport layer, on the hole transport layer, an emitting layer doped with 7% BD-052X (Idemitus) with a thickness of 45 nm was applied (herein, BD-052X was a blue fluorescent dopant, and an emitting host material was 9,10-di(naphthalene-2-anthracene (AND)).

For measurement of a phosphorescent host material, a phosphorescent material was deposited to film-form an emitting layer. At the same time, as a phosphorescent Ir metal complex dopant, tris(2-phenylpyridine)iridium (hereinafter, referred to as Ir(ppy)$_3$) was added. Herein, in the emitting layer, the concentration of Ir(ppy)$_3$ was 10 wt %. As a hole blocking layer, (1,1-bisphenyl)-4-olato)bis(2-methyl-8-quinolinolato)aluminum (hereinafter, referred to as BAlq) was vacuum-deposited with a thickness of 10 nm, and then as an electron injection layer, tris(8-quinolinol)aluminum (hereinafter, referred to as Alq$_3$) was film-formed with a thickness of 40 nm. Then, LiF (alkali-metal halide) was deposited with a thickness of 0.2 nm, and Al was deposited with a thickness of 150 nm. The Al/LiF was used as a cathode while the organic electro-luminescence device was fabricated.

Comparison Test Example

In order to compare to the case where the inventive compounds were used as hole transport layers, instead of the inventive compound, the compound represented by Formula 5 below (hereinafter, referred to as NPD) was used as a hole transport material so as to fabricate an organic electro-luminescence device with the same structure as that of Test Example.

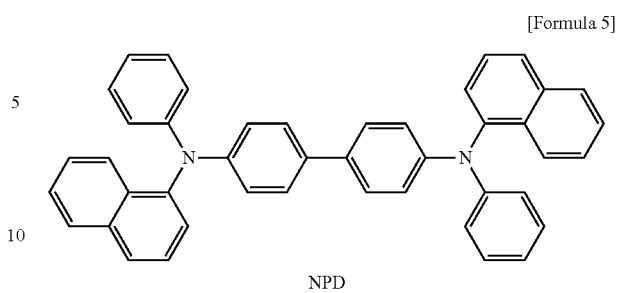

[Formula 5]

NPD

TABLE 1

| hole transport material | voltage (V) | current density (mA/cm$^2$) | luminous efficiency (cd/A) | chromaticity coordinates (x, y) |
|---|---|---|---|---|
| Example 1 | Compound A-4 | 6.1 | 12.92 | 9.4 | (0.15, 0.13) |
| Example 2 | Compound A-26 | 6.0 | 12.80 | 9.5 | (0.15, 0.13) |
| Example 3 | Compound B-20 | 5.8 | 12.70 | 9.9 | (0.15, 0.14) |
| Example 4 | Compound B-26 | 5.7 | 12.72 | 9.8 | (0.15, 0.14) |
| Comparative Example 1 | NPB | 7.2 | 13.35 | 7.5 | (0.15, 0.15) |

From the results noted in Table 1, it can be seen that in an organic electro-luminescence device using the inventive material for the organic electro-luminescence device, it is possible to obtain long-life blue light with a high efficiency, and an improved color purity. Thus, the inventive material as a hole transport material for an organic electro-luminescence device can lower a driving voltage, and significantly improve the luminous efficiency and life span.

It is natural that even though the inventive compounds are employed in other organic material layers of an organic electro-luminescence element, e.g., an emitting layer, an emission assisting layer, an electron injection layer, an electron transport layer and a hole injection layer as well as a hole transport layer, it is possible to achieve the same effects.

In the above, although the embodiments of the present invention have been described with reference to the accompanying drawings, a person skilled in the art should apprehend that the present invention can be embodied in other specific forms without departing from the technical spirit or essential characteristics thereof. Thus, the embodiments described above should be construed as exemplary in every aspect and not limiting. Furthermore, the scope of the present invention is defined by the appended claims rather than the above detailed description. Thus, the present invention should be construed to cover all modifications or variations induced from the meaning and range of the appended claims and their equivalents.

CROSS-REFERENCE TO RELATED APPLICATION

This application claims priority from and the benefit under 35 U.S.C. §119(a) of Korean Patent Application No. 10-2010-0014964, filed on Feb. 19, 2010, which is hereby incorporated by reference for all purposes as if fully set forth herein. Further, this application claims the benefit of priority in other countries than U.S., which are hereby incorporated by reference herein.

The invention claimed is:

1. A compound represented by Formula below,

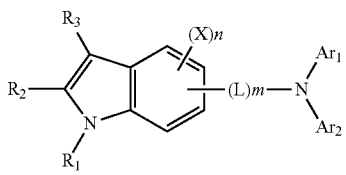

wherein (1) R1 to R3 and X are the same or different, and each independently represents (1) a $C_6$~$C_{60}$ aryl group or a $C_5$~$C_{60}$ heterocyclic group substituted or unsubstituted with at least one selected from the group including hydrogen, a halogen group, a cyano group, a nitrile group, a $C_1$~$C_{60}$ alkyl group, a $C_1$~$C_{60}$ alkoxy group, a $C_1$~$C_{60}$ alkylamine group, a $C_1$~$C_{60}$ arylamine group, a $C_1$~$C_{60}$ alkylthiophene group, a $C_6$~$C_{60}$ arylthiophene group, a $C_2$~$C_{60}$ alkenyl group, a $C_2$~$C_{60}$ alkynyl group, a $C_3$~$C_{60}$ cycloalkyl group, a $C_6$~$C_{60}$ aryl group, a deuterium-substituted $C_6$~$C_{60}$ aryl group, a $C_8$~$C_{60}$ arylalkenyl group, a substituted or unsubstituted silane group, a substituted or unsubstituted boron group, a substituted or unsubstituted germanium group, and a substituted or unsubstituted $C_5$~$C_{60}$ heterocyclic group; an amino group substituted with at least one substituent selected from the group including a substituted or unsubstituted aryl group, a substituted or unsubstituted arylalkyl group, and a substituted or unsubstituted arylalkenyl group; a fused cyclic group of a $C_6$~$C_{60}$ aromatic ring with a $C_4$~$C_{60}$ aliphatic ring; or any group selected from the group consisting of a hydrogen atom, a halogen atom, a nitro group, a cyano group, a substituted or unsubstituted aliphatic hydrocarbon group, a substituted or unsubstituted aryl group, and a substituted or unsubstituted hetero aryl group;

(2) n represents an integer of 1 to 3;

(3) Ar1 to Ar2 are the same or different, and each is independently selected from the group including: a $C_1$~$C_{60}$ alkyl group, a $C_1$~$C_{60}$ alkoxy group, a $C_1$~$C_{60}$ aryl group, a carbazolyl group, or a fluorenyl group, substituted or unsubstituted with at least one substituent selected from the group including a halogen group, an alkyl group, an alkenyl group, a substituted or unsubstituted aryl group, a substituted or unsubstituted arylalkyl group, a substituted or unsubstituted arylalkenyl group, a substituted or unsubstituted hetero cyclic group, a substituted or unsubstituted carbazolyl group, a substituted or unsubstituted fluorenyl group, a nitrile group, and an acetylene group, or a hetero cyclic group that is substituted or unsubstituted with at least one substituent selected from the group including a halogen group, an alkyl group, an alkenyl group, an alkoxy group, a substituted or unsubstituted arylamine group, a substituted or unsubstituted aryl group, a substituted or unsubstituted carbazolyl group, a substituted or unsubstituted fluorenyl group, a nitrile group, and an acetylene group and comprises O, N, or S as a heteroatom; a hydroxyl group; a carboxyl group; a nitrile group, a nitro group, a halogen group, —N(R')(R"); —CO—N(R')(R"); and —COOR'; and (4) L represents a substituted or unsubstituted arylene group, a substituted or unsubstituted hetero arylene group, a group selected from the group including divalent or trivalent, substituted or unsubstituted aliphatic hydrocarbons, or a divalent linking group, and m represents an integer of 0 to 3.

2. The compound according to claim 1, wherein in Formula above, when L is a simple linking group, the compound is represented by Formula below

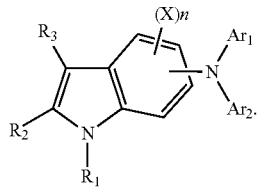

3. The compound according to claim 1, wherein in Formula above, when L has a substituted or unsubstituted group, the compound is represented by Formula below

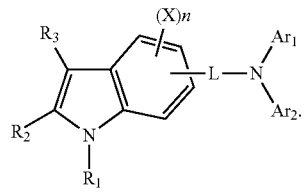

4. The compound according to claim 1, wherein X and R1 to R3 form a ring together with an adjacent group, and Ar1 to Ar2 form an aliphatic or hetero fused ring together with an adjacent group.

5. An organic electronic element comprising one or more organic material layers comprising the compound according to claim 1.

6. The organic electronic element according to claim 5, wherein the organic material layers are formed by a soluble process of the compound.

7. The organic electronic element according to claim 5, wherein the organic electronic element is an organic electroluminescence element in which a first electrode, said one or more organic material layers, and a second electrode are sequentially layered.

8. The organic electronic element according to claim 7, wherein the organic material layers comprise any one of a hole injection layer, a hole transport layer, an emitting layer, an electron transport layer, and an electron injection layer.

9. The organic electronic element according to claim 7, wherein the organic material layers comprise an emission assisting layer, and the emission assisting layer comprises the compound.

10. A terminal comprising a display device and a control part for driving the display device, the display device comprising the organic electronic element according to claim 7.

11. The terminal according to claim 10, wherein the organic electronic element is any one of an organic light emitting diode (OLED), an organic solar cell, an organic photo conductor (OPC) drum, and an organic transistor (organic TFT).

* * * * *